United States Patent
Xu

(10) Patent No.: US 9,157,901 B2
(45) Date of Patent: Oct. 13, 2015

(54) METHOD FOR MEASURING MOISTURE IN LIQUID CRYSTALS

(71) Applicant: SHENZHEN CHINA STAR OPTOELECTRONICS TECHNOLOGY CO., LTD., Shenzhen (CN)

(72) Inventor: Rui Xu, Shenzhen (CN)

(73) Assignee: SHENZHEN CHINA STAR OPTOELECTRONICS TECHNOLOGY CO., LTD., Shenzhen (CN)

( * ) Notice: Subject to any disclaimer, the term of this patent is extended or adjusted under 35 U.S.C. 154(b) by 8 days.

(21) Appl. No.: 14/233,769

(22) PCT Filed: Nov. 22, 2013

(86) PCT No.: PCT/CN2013/087682
§ 371 (c)(1),
(2) Date: Jan. 20, 2014

(87) PCT Pub. No.: WO2015/070479
PCT Pub. Date: May 21, 2015

(65) Prior Publication Data
US 2015/0140667 A1    May 21, 2015

(30) Foreign Application Priority Data
Nov. 15, 2013  (CN) .......................... 2013 1 0572345

(51) Int. Cl.
*G01N 31/16* (2006.01)
*G01N 31/00* (2006.01)
*G01N 21/81* (2006.01)
*G01N 21/75* (2006.01)
*G01N 31/22* (2006.01)
*G01N 33/00* (2006.01)

(52) U.S. Cl.
CPC .............. *G01N 31/168* (2013.01); *G01N 31/00* (2013.01); *G01N 21/75* (2013.01); *G01N 31/16* (2013.01); *G01N 31/222* (2013.01); *G01N 33/00* (2013.01); *G01N 2033/0095* (2013.01)

(58) Field of Classification Search
CPC ..... G01N 31/168; G01N 31/16; G01N 31/00; G01N 31/222; G01N 31/21; G01N 21/81; G01N 21/78; G01N 21/77; G01N 21/75; G01N 21/00
USPC .............................................. 436/42, 390, 39
See application file for complete search history.

(56) References Cited

PUBLICATIONS

STN Search obtain on Mar. 17, 2015, pp. 1-10.*

* cited by examiner

*Primary Examiner* — Christine T Mui
(74) *Attorney, Agent, or Firm* — Mark M. Friedman

(57) ABSTRACT

When measuring the liquid crystals to he measured, the present invention adding the liquid crystals under test to a mixed solvent to form a solvent to be measured; measuring the moisture in the liquid crystal measurement sample through a reaction reagent to achieve a measurement result; wherein the mixed solvent comprises a first solvent, and the first solvent is dissolved with the methanol of the reaction reagent mutually and dissolves the liquid crystals to be measured. In the present invention, the moisture in the liquid crystal can be fully released and achieve accurate measurements.

17 Claims, 2 Drawing Sheets

METHOD FOR MEASURING MOISTURE IN LIQUID CRYSTALS

FIELD OF THE INVENTION

The present invention relates to a technical field of manufacturing liquid crystals, and in particular to a method for measuring the moisture in liquid crystals.

BACKGROUND OF THE INVENTION

LCD (liquid crystal display) technology has obvious advantages, such as a low driving voltage, a low power consumption, a high reliability, a huge information-displaying amounts, a color display, a flicker-free, a low cost, a capability of being made into various sizes and types LCD displayer, a convenience of portability and so on. Because of these above advantages, LCD technology has a great influence on the product structures for imaging displays, thereby facilitating developments of microelectronics and optoelectronic information technology. With continuous development of LCD technology, the demand for liquid crystal display panels is also increasing.

The liquid crystal, which is in a state between liquid and crystalline, is the core material for LCD technology. The liquid crystal has some properties of both a liquid state and a crystalline state (such as fluidity, anisotropy, etc.), as well as its own unique properties. For example, after the power is turned on, the liquid crystal becomes orderly arranged to enable lights to pass therethrough easily, whereas after the power is turned off, the liquid crystal is arranged chaotically to prevent the lights from passing therethrough. Based on the above characteristics, a liquid crystal layer comprising liquid crystals can be made, and the liquid crystal layer is disposed inside an LCD panel. When a light beam passes through the liquid crystal layer, the liquid crystals of the liquid crystal layer become orderly arranged or chaotically arranged, according to the circumstances of the electricity passing, so as to allow lights to pass therethrough or block the lights and then display the corresponding images. Therefore, an outstanding image definition greatly depends on the merits or demerits of the liquid crystal characteristics.

In a case of a moisture content ratio for the liquid crystals, during an actual production process, the moisture content ratio in the liquid crystal material has a higher requirement. Generally, the moisture content ratio has a requirement of less than 10 ppm (parts per million concentration). A higher moisture content ratio will reduce the impedances of the liquid crystals, thereby lowering a voltage holding ratio of the liquid crystal panel which would invoke an image defect such as an IS (Image Sticking). Therefore, the measurement and control of the moisture content ratio in the liquid crystals brings a significant effect on the LCD technology.

In prior art, a primary method of measuring the moisture content ratio of the liquid crystals is 'Karl-Fischer' method (referred to as KF), which mainly applies a Karl-Fisher reagent on a liquid crystal sample to measure its moisture content ratio, wherein the Karl-Fisher reagent includes $SO_2$, $I_2$, organic alkali and an alcohol solvent. The measurement principle of the Karl-Fischer method is given in the following formulas:

$$I_2 + SO_2 + 2H_2O \rightarrow 2HI + H_2SO_4 \quad (1)$$

$$C_5H_5N + H_2O + I_2 + SO_2 \rightarrow 2C_5H_5N \cdot HI + C_5H_5N \cdot SO_3 \quad (2)$$

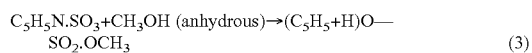

$$C_5H_5N \cdot SO_3 + CH_3OH \text{ (anhydrous)} \rightarrow (C_5H_5 + H)O\text{—}SO_2 \cdot OCH_3 \quad (3)$$

In which $SO_2$ and $I_2$ are oxidation-reduction reactions with the moistures of the liquid crystal sample, quantitatively. The chemical relationship is a quantitative basis of the moistures in the sample. The organic base is mostly pyridine, which is used to neutralize the acid generated during the reaction and to perform the reaction toward a right direction. The alcohols, mostly methanol, are mainly used to react with the unstable sulfuric anhydride pyridine generated in the reaction, and to form a stable Methyl sulfate pyridine, treated as a reaction medium.

Please refer to FIG. 1. A liquid crystal sample with a quantitative amount is drawn by a syringe to infuse into the Karl-Fisher cuvette containing the Karl-Fisher reagent for directly conducting the reaction, the end of which is indicated and monitored through a double-platinum indicator electrode within an instrument. However, in the research process the inventor of the present invention found that the liquid crystals mostly contain some substances with low polarity, such as a benzene ring or cyclohexane, which are not compatible with the methanol system with medium polarity of the Karl-Fisher reagent and easily exist in the form of dough insolubles that are not beneficial to release and test the moistures in the liquid crystals. This greatly reduces the accuracy of the test of the moisture contents in the liquid crystals. With the lower moisture content of the liquid crystal sample, it's difficult to release trace of the moistures wrapped in the liquid crystals, which easily results in moisture content measurement errors. This will eventually lead to adverse LCD panel displays after the formation of a liquid crystal panel.

Therefore, there is a need to solve the above problems of the prior art.

SUMMARY OF THE INVENTION

In view of this, the present invention is to provide a method for measuring moistures in liquid crystals for solving the technical drawbacks of the prior art in hardly releasing traces of moisture in a liquid crystals, which causes the larger measurement errors of the moisture content ratio in the liquid crystal, thereby affecting an image-displaying quality of the liquid crystal panel.

In order to solve the drawbacks of the prior art, the present invention provides a method for measuring moisture in liquid crystals comprising:

measuring the liquid crystals under test;
adding the liquid crystals under test to a mixed solvent, thereby dissolving the liquid crystals under test to form a solvent under test;
measuredly taking a liquid crystal measurement sample from the solvent under test, and measuring the moisture in the liquid crystal measurement sample through a reaction reagent to achieve a measurement result,
wherein the reaction reagent comprises methanol, the mixed solvent comprises a first solvent, the first solvent can dissolve with the methanol of the reaction reagent mutually and can dissolve the liquid crystals under test.

In the above-described method, the first solvent is isopropanol.

In the above-described method, the mixed solvent further comprises a second solvent which dissolves the liquid crystals under test and reduces the viscosity of the isopropanol of the solvent under test.

In the above-described method, before adding the liquid crystals under test to the mixed solvent, the method further comprises a step of:

adding the first solvent and the second solvent into a first hermetic container and homogeneously mixing the first solvent and the second solvent to form a first mixed solvent; wherein the volume of the second solvent is less than or equal to ¼the volume of the first solvent in the first mixed solvent.

In the above-described method, the moisture content of both the first solvent and the second solvent are less than or equal to a first threshold value, and the range of the first threshold value is from 0.02% to 0.06%.

In the above-described method, after measuring the liquid crystals under test, pouring the liquid crystals under test in a second hermetic container, the color of which is brown.

In the above-described method, after forming the first mixed solvent, the method further comprises the steps of:
  adding a first predetermined amount of the first mixed solvent to the second hermetic container, and mixing homogeneously the first mixed solvent by a stirring bar to form a second mixed solvent;
  pouring the second mixed solvent in a volumetric flask; and
  rinsing the second hermetic container and the stirring bar through the remainder of the first mixed solvent of the first hermetic container, and pouring a rinsed first mixed solvent into the volumetric flask to form a third mixed solvent.

In the above-described method, after forming the third mixed solvent, the method further comprises the steps of:
  adding the remainder of the first mixed solvent of the first hermetic container into the volumetric flask containing the third mixed solvent to form the solvent under test;
  measuredly taking the liquid crystal measurement sample from the solvent under test, and measuring the moisture content of the liquid crystal measurement sample by the reaction reagent to achieve the measurement result.

In the above-described method, the mass of the liquid crystal measurement sample is greater than or equal to a second threshold value, the range of the second threshold value is between 0.8 g to 1.5 g.

In the above-described method, the second solvent is n-hexane.

In the embodiment of the present invention, a method of adding a mixed solvent in advance thereinto is applied, which dissolves the liquid crystal in advance by adding an amount of the mixed solvent before the reaction, then pouring to the Karl-Fisher cuvette to conduct the reaction. The first solvent of the mixed solvent can dissolve with the methanol of the Karl-Fisher reagent mutually and can also dissolve the liquid crystals. The second solvent is a hydrocarbon solvent, and not only can dissolve the liquid crystal but also can reduce the viscosity of the isopropanol. The liquid crystals under test in the present invention exist with the form of liquid crystal molecules in Karl-Fisher reagent. It is able to overcome the drawbacks of the conventional method that the moisture in the liquid crystal that can not be fully released. Thus, this can release moisture completely to achieve accurate measurements, and by a simple operation can increase the accuracy of the measurement of measuring moisture in liquid crystals.

The preferred embodiments adopted by the present invention to achieve the above and other objects can be best understood by referring to the following detailed description of the preferred embodiments and the accompanying drawings.

DETAILED DESCRIPTION OF THE PREFERRED EMBODIMENTS

Figure 1:
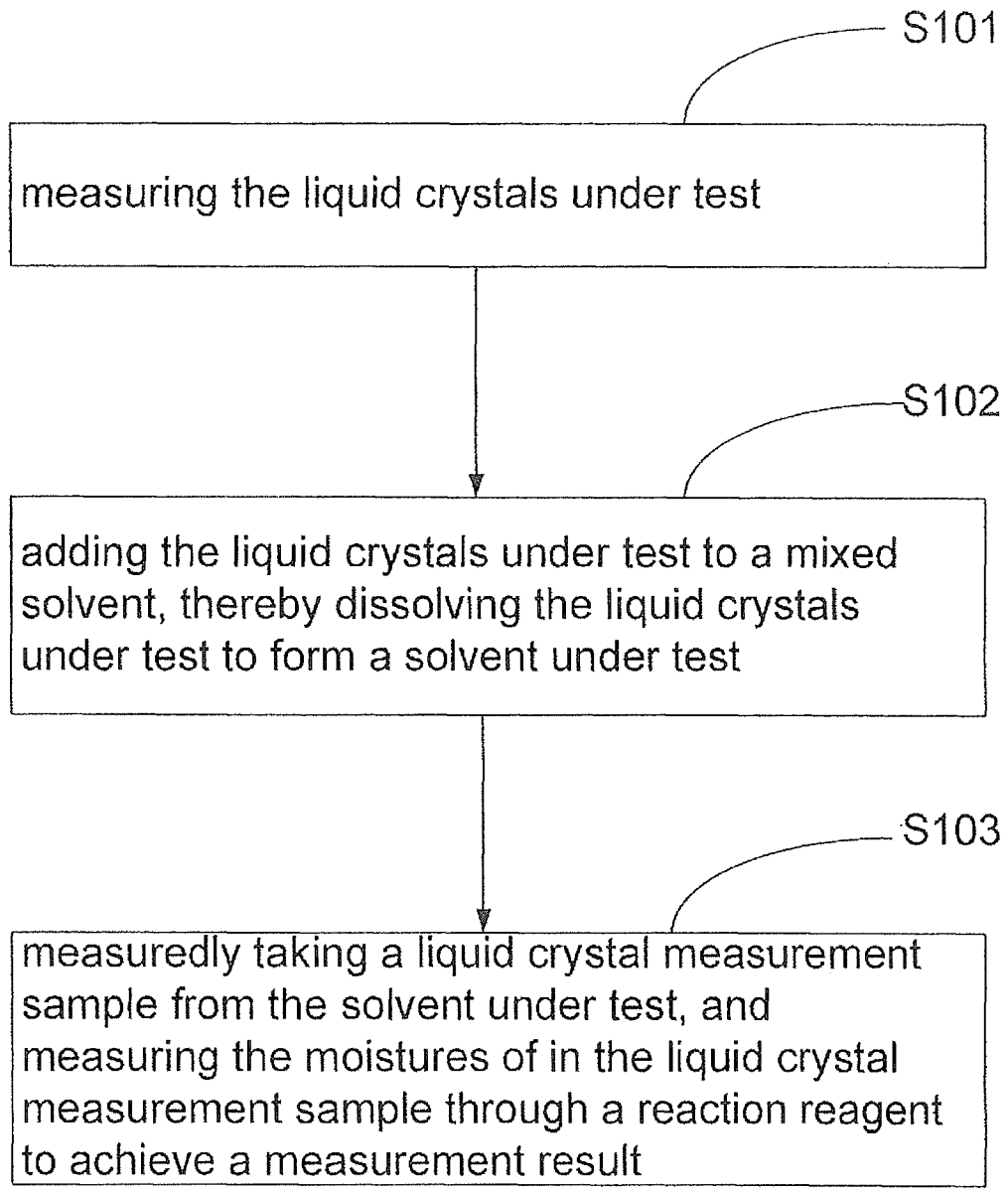
FIG. 1 is a schematic flowchart of a method for measuring moisture in liquid crystals according to a first preferred embodiment of the present invention.

The method adopted by the present invention to achieve the above and other objects can be best understood by referring to the following detailed description of the preferred embodiments and the accompanying drawings. Furthermore, directional terms described by the present invention, such as upper, lower, front, back, left, right, inner, outer, side, longitudinal/vertical, transverse/horizontal, etc., are only directions by referring to the accompanying drawings, and thus the used directional terms are used to describe and understand the present invention, but the present invention is not limited thereto. In the drawings, similar structural elements use the same reference numerals.

Referring now to FIG. 1, which is a schematic flowchart of a method for measuring moisture in liquid crystals according to a first preferred embodiment of the present invention.

In step S101, the liquid crystals under test are measured.

In step S102, the liquid crystals under test are added into a mixed solvent, thereby dissolving the liquid crystals under test to form a solvent under test, wherein the mixed solvent comprises a first solvent.

Optionally, the first solvent is isopropanol or other chemical substances as long as it can dissolve with methanol mutually and also can dissolve the liquid crystal, the whole of which are within the scope of the present invention.

In step S103, a liquid crystal measurement sample is measuredly taken from the solvent under test, and the moisture of the liquid crystal measurement sample is measured through a reaction reagent for achieving a measurement result.

Wherein the reaction reagent comprises methanol, the mixed solvent comprises a second solvent, the first solvent can dissolve with the methanol of the reaction reagent mutually and can dissolve the liquid crystals under test, and the second solvent can dissolve the liquid crystals under test and reduces the viscosity of the isopropanol of the solvent under test.

Specifically, the steps of adding the liquid crystals under test to a mixed solvent and thereby dissolving the liquid crystals under test to form the solvent under test further comprise:
  a) adding the first solvent and the second solvent into a first hermetic container and homogeneously mixing the first solvent and the second solvent to form a first mixed solvent; wherein the volume of the second solvent is less than or equal to ¼the volume of the first solvent in the first mixed solvent, the moisture content of both the first solvent and the second solvent are less than or equal to a first threshold value, and the range of the first threshold value is from 0.02% to 0.06%.
  b) pouring the liquid crystals under test in a second hermetic container, wherein the color of the second hermetic container is brown.
  c) adding a first predetermined amount of the first mixed solvent to the second hermetic container, and mixing homogeneously the first mixed solvent by a stirring bar to form a second mixed solvent.
  d) pouring the second mixed solvent in a volumetric flask, and rinsing the second hermetic container and the stirring bar through the remainder of the first mixed solvent of the first hermetic container, and pouring a rinsed first mixed solvent into the volumetric flask to form a third mixed solvent.

e) adding the remainder of the first mixed solvent of the first hermetic container into the volumetric flask containing the third mixed solvent to form a fourth mixed solvent, wherein the fourth mixed solvent is the solvent under test in this embodiment of the present invention.

f) measuredly taking the liquid crystal measurement sample from the fourth mixed solvent (the solvent under test), and measuring the moisture content of the liquid crystal measurement sample by the reaction reagent to achieve the measurement result, wherein the mass of the liquid crystal measurement sample is greater than or equal to a second threshold value, the range of the second threshold value is between 0.8 g to 1.5 g, 1 g is preferably.

Wherein the first solvent is preferably isopropanol, the second solvent is a hydrocarbon solvent, such as n-hexane preferably.

In this embodiment of the present invention, the mixed solvent comprises the first solvent and the second solvent, the first solvent dissolves with the methanol of the reaction reagent mutually, and dissolves the liquid crystals under test, the second solvent dissolves the liquid crystals under test and also reduces the viscosity of the isopropanol of the hydrocarbon solvent.

In the embodiment of the present invention, a method of adding a mixed solvent in advance thereinto is applied, which dissolves the liquid crystal in advance by adding an amount of the mixed solvent before the reaction, then pouring to the Karl-Fisher cuvette for making reaction. The first solvent (isopropanol) of the mixed solvent can dissolve with the methanol of the Karl-Fisher reagent mutually and also can dissolve the liquid crystal. The second solvent is a hydrocarbon solvent and not only can dissolve the liquid crystal but also can reduce the viscosity of the isopropanol, such as n-hexane, cyclohexane, cyclopentane, and heptane, Also, the percentage of volume of the second solvent in the mixed solvent is less than or equal to 20% for preventing the solvent stratified. The liquid crystals under test of the present invention exist with the form of liquid crystal molecules in Karl-Fisher reagent. It is able to overcome the drawback of the conventional method that the moisture in the liquid crystal can not be fully released. Thus, this can release moisture completely to achieve accurate measurements, and by a simple operation can increase the accuracy of the measurement of measuring moisture in liquid crystals.

Figure 2:
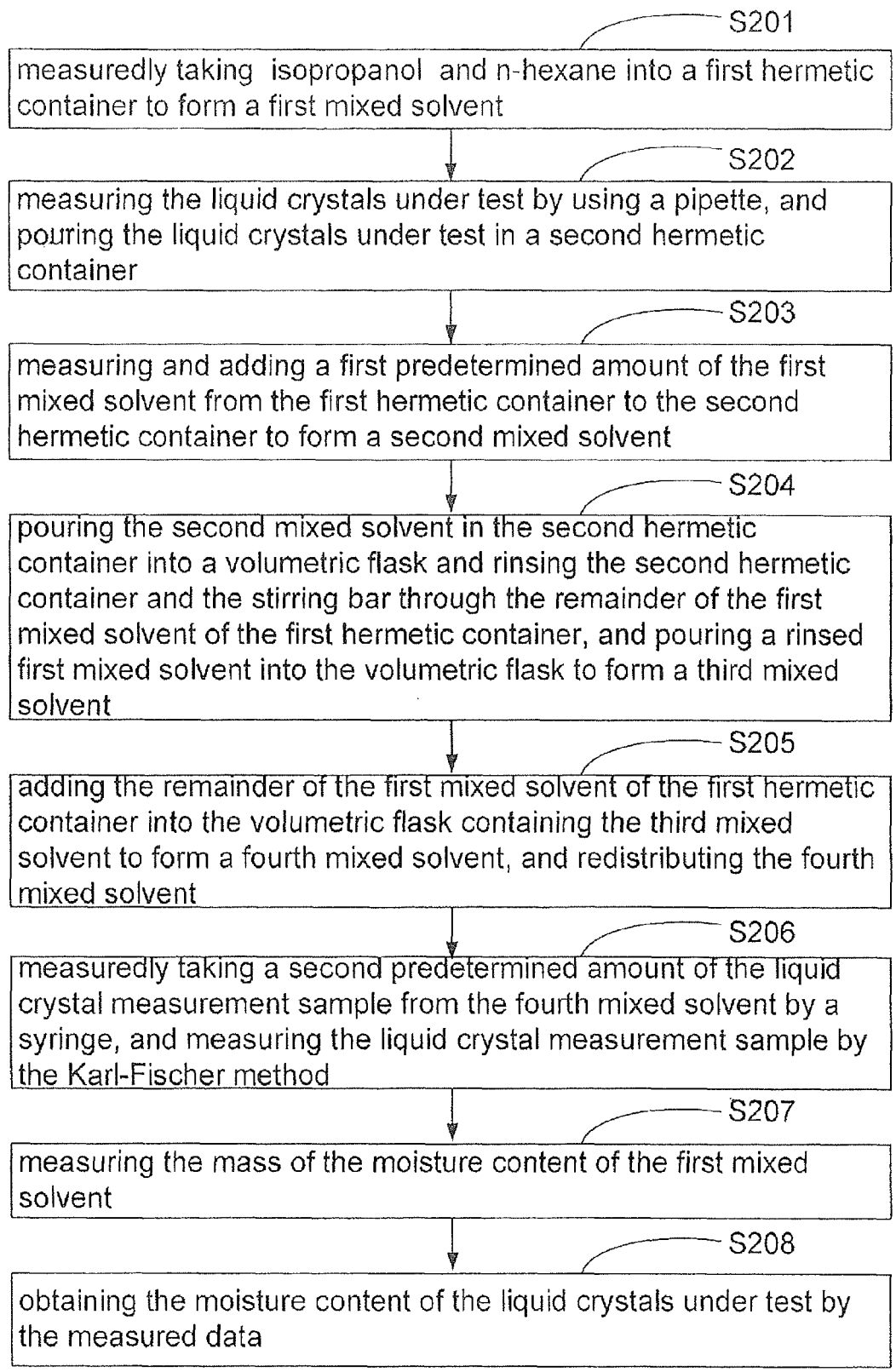
FIG. 2 is a schematic flowchart of a method for measuring moisture in liquid crystals according to a second preferred embodiment of the present invention.

Referring to the FIG. 2, which is a schematic flowchart of a method for measuring moisture in liquid crystals according to a second preferred embodiment of the present invention, wherein the first solvent is isopropanol and the second solvent is n-hexane, for example.

In step S201, isopropanol and n-hexane are measuredly taken, and the measured isopropanol and n-hexane are added into a first hermetic container and the first solvent and the second solvent are homogeneously mixed to form a first mixed solvent.

The isopropanol is chromatographically pure isopropanol. The volume of isopropanol measured in step S201 is $V_1$ (ml), and the water content of the isopropanol is less than or equal to a first threshold value, and the range of the first threshold value is 0.02% to 0.06%, 0.05%, preferably. The n-hexane is chromatographically pure n-hexane. The volume of n-hexane measured in step S201 is $V_2$ (ml), and the water content of the n-hexane is less than or equal to the first threshold value, and the range of the first threshold value is 0.02% to 0,06%, 0.05%, preferably.

In step S202, the liquid crystals under test is measuredly taken by using a pipette, and then the liquid crystals under test is poured in a second hermetic container.

The color of the second hermetic container is brown for avoiding the liquid crystal being irradiated by the lights. The second hermetic container is disposed with a stirring bar therein. In step S202, the volume of liquid crystals under test is $V_3$ (ml), and the mass of liquid crystals under test is $M_1$ (g).

In step S203, the first mixed solvent is measuredly taken in a first predetermined amount thereof from the first hermetic container, the first mixed solvent with the first predetermined amount is added into the second hermetic container, and by the stirring bar, the liquid crystals under test and the mixed solvent are mixed homogeneously to fully dissolve, thereby forming a second mixed solvent.

The first predetermined amount of the first mixed solvent is $V_4$ (ml), in the actual embodiment of the present invention, $V_4 < 2V_3/3$.

In the embodiment of the present invention, the volume $V_2$ of n-hexane is less than or equal to ¼ the volume $V_1$ of the isopropanol in the first mixed solvent, that is $V_2 \leq V_1/4$. This ensures that the liquid crystals under test can be fully dissolved in the first mixed solvent, and it also can avoid the liquid crystals under test becoming stratified in methanol following the test reagent due to the ratio of the n-hexane too being large, and further can reduce the viscosity of the first mixed solvent.

In step S204, the second mixed solvent is poured in the second hermetic container into a volumetric flask, and the second hermetic container and the stirring bar is rinsed through the remainder of the first mixed solvent of the first hermetic container, and a rinsed first mixed solvent into the volumetric flask is poured to form a third mixed solvent.

The volume of the volumetric flask is $V_5$, wherein the $V_5$ is approximately equal to $2V_3$ for ensuring the concentration of the liquid crystals under test in the volumetric flask. The times for rinsing the second hermetic container and stirring the bar through the remainder of the first mixed solvent of the first hermetic container is 3, preferably.

In step S205, the remainder of the first mixed solvent of the first hermetic container is added into the volumetric flask containing the third mixed solvent to form a fourth mixed solvent, and the fourth mixed solvent is redistributed.

The volume of the fourth mixed solvent is $V_5$. Namely, the capacity of the volumetric flask is $V_5$, In step S205, the volumetric flask will be filled.

In step S206, the liquid crystal measurement sample is measuredly taken in a second predetermined amount from the fourth mixed solvent by a syringe, and the liquid crystal measurement sample is measured by the Karl-Fischer method.

For example, the syringe is a Karl-Fischer syringe. The volume of the liquid crystal measurement sample measured by the liquid crystal measurement sample is $V_6$. Then, the moisture content of the liquid crystal measurement sample measured by the Karl-Fischer moisture titrator is $M_2$ (g).

In the embodiment of the present invention, the second predetermined amount of the liquid crystal measurement sample is greater than or equal to a second threshold value, the range of the second threshold value is between 0.8 g to 1.5 g, 1 g, preferably.

In step S207, the mass of the moisture content of the first mixed solvent is measured.

For example, to provide another first mixed solvent and add another first mixed solvent into the volumetric flask. The liquid crystal measurement sample is measuredly taken and the is measuredly-taken liquid crystal measurement sample is measured by the Karl-Fischer method to achieve the mass $M_3$ (g) of the moisture content of the first mixed solvent.

In step S208, the moisture content of the liquid crystals under test is obtained by the measured data.

The formula of generating the moisture content of the liquid crystal to be measured as follows:

$$\frac{M_2 - M_3}{\frac{V_6}{V_5} \times M_1} \times 100\%$$

In the embodiment of the present invention, a method of adding a mixed solvent in advance thereinto is applied, which dissolves the liquid crystal in advance by adding an amount of the mixed solvent before the reaction, then pouring to the Karl-Fisher cuvette to response. The first solvent of the mixed solvent can dissolve with the methanol of the Karl-Fisher reagent mutually and can also dissolve the liquid crystal. The second solvent is a hydrocarbon solvent, and not only can it dissolve the liquid crystal, but is can also reduce the viscosity of the isopropanol. The liquid crystals under test of the present invention exist in the form of liquid crystal molecules in Karl-Fisher reagent. It is possible to overcome the drawback that the moisture in the liquid crystal that can not be fully released by the conventional method can thus release moisture completely to achieve accurate measurements, and by a simple operation increase the accuracy of the measurement of measuring moisture in liquid crystals.

As stated above, the present invention has been described with a preferred embodiment thereof and it is understood that many changes and modifications to the described embodiment can be carried out without departing from the scope and the spirit of the invention that is intended to be limited only by the appended claims.

What is claimed is:

1. A method for measuring moisture in liquid crystals comprising:
   providing the liquid crystals to be measured;
   adding the liquid crystals to be measured to a mixed solvent, thereby dissolving the liquid crystals to be measured to form a solvent to be measured;
   measuredly taking a liquid crystal measurement sample from the solvent to be measured pouring the liquid crystal measurement sample into a reaction reagent to conduct a reaction and measuring the moisture in the liquid crystal measurement sample through a the reaction reagent to achieve a measurement result;
   wherein the reaction reagent comprises methanol, the mixed solvent comprises isopropanol, the isopropanol is dissolved with the methanol of the reaction reagent mutually and dissolves the liquid crystals to be measured, the mixed solvent further comprises n-hexane, which dissolves the liquid crystals to be measured and reduces the viscosity of the isoproanol in the solvent to be measured;
   wherein the reaction reagent further comprises sulfur dioxide and iodine which are oxidation-reduction reactions with the moisture of the liquid crystal measurement sample for measuring the moisture content of the liquid crystal to be measured;
   wherein by dissolving the liquid crystals in advance via adding an amount of the mixed solvent before the reaction, the liquid crystal to be measured exists with a form of liquid crystal molecules and can release moisture in the mixed solvent completely.

2. The method for measuring moisture in liquid crystals according to Claim 1, wherein before adding the liquid crystals to be measured to the mixed solvent, the method further comprises a step of:
   adding an isopropanol and an n-hexane into a first hermetic container and homogeneously mixing the isopropanol and the n-hexane to form a first mixed solvent, wherein a volume of the n-hexane is less than or equal to ¼ a volume of the isopropanol in the first mixed solvent.

3. The method for measuring moisture in liquid crystals according to Claim wherein a moisture contents of both the isopropanol and the n-hexane are less than or equal to a first threshold value, and the range of the first threshold value is from 0.02% to 0.06%.

4. The method for measuring moisture in liquid crystals according to claim 2, wherein after providing the liquid crystals to be measured, pouring the liquid crystals to he measured in a second hermetic container, the color of which is brown.

5. The method for measuring moisture in liquid crystals according to claim 4, wherein after forming the first mixed solvent, the method further comprises the steps of;
   adding a first predetermined amount of the first mixed solvent to the second hermetic container, and mixing homogeneously the first mixed solvent by a stirring bar to form a second mixed solvent;
   pouring the second mixed solvent in a volumetric flask; and
   rinsing the second hermetic container and the stirring bar by the remainder of the first mixed solvent of the first hermetic container, and pouring a rinsed first mixed solvent into the volumetric flask to form a third mixed solvent.

6. The method for measuring moisture in liquid crystals according to claim 5, wherein after forming the third mixed solvent, the method further comprises the steps of:
   adding the remainder of the first mixed solvent of the first hermetic container into the volumetric flask containing the third mixed solvent to form the solvent to be measured; and
   measuredly taking the liquid crystal measurement sample from the solvent to be measured, and measuring the moisture content of the liquid crystal measurement sample by the reaction reagent to achieve the measurement result;
   wherein the reaction reagent further comprises sulfur dioxide and Iodine which are oxidation-reduction reactions with the moisture of the liquid crystal measurement sample for measuring the moisture content of the liquid crystal to be measured.

7. The method for measuring moisture in liquid crystals according to claim 6, wherein a mass of the liquid crystal measurement sample is greater than or equal to a second threshold value, the range of the second threshold value is between 0.8 g to 1.5 g.

8. A method for measuring moisture in liquid crystals comprising:
   providing the liquid crystals to be measured;
   adding the liquid crystals to be measured to a mixed solvent, thereby dissolving the liquid crystals to he measured to form a solvent to be measured;
   measuredly taking a liquid crystal measurement sample from the solvent to be measured, pouring the liquid crystal measurement sample into a reaction reagent to conduct a reaction and measuring the moisture of the liquid crystal measurement sample through a reaction reagent fur achieving a measurement result, wherein the reaction reagent comprises methanol, the mixed solvent comprises a first solvent, and the first solvent is dissolved with the methanol of the reaction reagent mutually and dissolves the liquid crystals to be measured;

wherein the reaction reagent further comprises sulfur dioxide and Iodine which are oxidation-reduction reactions with the moisture of the liquid crystal measurement sample for measuring the moisture content of the liquid crystal to he measured;

wherein by dissolving the liquid crystals in advance via adding an amount of the mixed solvent before the reaction, the liquid crystal to be measured exists with a form of liquid crystal molecules and can release moisture in the mixed solvent completely.

9. The method for measuring moisture in liquid crystals according to claim 8, wherein the first solvent is isopropanol.

10. The method for measuring moisture in liquid crystals according to claim 9, wherein the mixed solvent further comprises a second solvent which dissolves the liquid crystals to be measured and reduces the viscosity of the isopropanol of the solvent to be measured.

11. The method for measuring moisture in liquid crystals according to claim 10, wherein, before adding the liquid crystals to be measured to the mixed solvent, the method further comprises a step of:

adding a first solvent and a second solvent into a first hermetic container and homogeneously mixing the first solvent and the second solvent to form a first mixed solvent; wherein a volume of the second solvent is less than or equal to ¼a volume of the first solvent in the first mixed solvent.

12. The method for measuring moisture in liquid crystals according to claim 10, wherein a moisture contents of both the first solvent and the second solvent are less than or equal to a first threshold value, and the range of the first threshold value is from 0.02% to 0.06%.

13. The method for measuring moisture in liquid crystals according to claim 11, wherein after providing the liquid crystals to be measured, pouring the liquid crystals to be measured in a second hermetic container, the color of which is brown.

14. The method for measuring moisture in liquid crystals according to claim 13, wherein after forming the first mixed solvent, the method further comprises the steps of:

adding a first predetermined amount of the first mixed solvent to the second hermetic container, and mixing homogeneously the first mixed solvent by a stirring bar to form a second mixed solvent;

pouring the second mixed solvent in a volumetric flask; and rinsing the second hermetic container and the stirring bar through the remainder of the first mixed solvent of the first hermetic container, and pouring a rinsed first mixed solvent into the volumetric flask to form a third mixed solvent.

15. The method for measuring moisture in liquid crystals according to claim 13, wherein after forming the third mixed solvent, the method further comprises the steps of:

adding the remainder of the first mixed solvent of the first hermetic container into the volumetric flask containing the third mixed solvent to form the solvent to be measured;

measuredly taking the liquid crystal measurement sample from the solvent to be measured, and measuring the moisture content of the liquid crystal measurement sample by the reaction reagent to achieve the measurement result;

wherein the reaction reagent further comprises sulfur dioxide and iodine which are oxidation-reduction reactions with the moisture of the liquid crystal measurement sample for measuring the moisture content of the liquid crystal to be measured.

16. The method for measuring moisture in liquid crystals according to claim 13, wherein a mass of the liquid, crystal measurement sample is greater than or equal to a second threshold value, the range of the second threshold value is between 0.8 g to 1.5 g.

17. The method for measuring moisture in liquid crystals according to claim 10, wherein the second solvent is n-hexane.

* * * * *

UNITED STATES PATENT AND TRADEMARK OFFICE
CERTIFICATE OF CORRECTION

PATENT NO. : 9,157,901 B2  
APPLICATION NO. : 14/233769  
DATED : October 13, 2015  
INVENTOR(S) : Rui Xu Page 1 of 1

It is certified that error appears in the above-identified patent and that said Letters Patent is hereby corrected as shown below:

In the claims:

Column 8 Claim 3 line 16 should be corrected as follows:
Change
-- to Claim --
to
"to Claim 1"

Signed and Sealed this  
Fifteenth Day of March, 2016

Michelle K. Lee  
*Director of the United States Patent and Trademark Office*